(12) United States Patent
Wachter et al.

(10) Patent No.: US 8,801,980 B2
(45) Date of Patent: Aug. 12, 2014

(54) DEVICE AND METHOD FOR PRODUCTION OF DENTAL MOLDED PARTS

(75) Inventors: Wolfgang Wachter, Schaan (LI); Walter Pokorny, Gais (AT); Gottfried Rohner, Altstätten (CH); Robert Grünenfelder, Eschen (LI)

(73) Assignee: Ivoclar Vivadent AG, Schaan (LI)

( * ) Notice: Subject to any disclaimer, the term of this patent is extended or adjusted under 35 U.S.C. 154(b) by 363 days.

(21) Appl. No.: 11/899,969

(22) Filed: Sep. 6, 2007

(65) Prior Publication Data

US 2008/0093758 A1    Apr. 24, 2008

(30) Foreign Application Priority Data

Sep. 6, 2006    (DE) .................. 10 2006 041 786

(51) Int. Cl.
*A61C 13/00*    (2006.01)

(52) U.S. Cl.
USPC ............... 264/16; 264/17; 264/18; 264/19; 264/20

(58) Field of Classification Search
USPC .......................... 264/16, 17, 18, 19
See application file for complete search history.

(56) References Cited

U.S. PATENT DOCUMENTS

| 2,266,957 | A | * | 12/1941 | Chenoweth | 219/395 |
| 2,806,253 | A | | 9/1957 | Vernon et al. | |
| 3,988,094 | A | | 10/1976 | McGowan et al. | |
| 5,040,964 | A | | 8/1991 | Oppawsky et al. | |
| 5,672,305 | A | * | 9/1997 | Kogure | 264/102 |
| 5,997,293 | A | | 12/1999 | Grunenfelder et al. | |
| 6,186,761 | B1 | * | 2/2001 | Petkow et al. | 425/178 |
| 2004/0197736 | A1 | * | 10/2004 | Knott | 433/167 |
| 2005/0011885 | A1 | | 1/2005 | Seghatol et al. | |

FOREIGN PATENT DOCUMENTS

| DE | 83 20 883 U1 | 11/1983 |
| DE | 39 10 438 C2 | 10/1990 |
| DE | 102 08 801 C1 | 6/2003 |
| DE | 103 31 863 B3 | 10/2004 |
| DE | 103 24 404 A1 | 12/2004 |
| DE | 103 27 892 B3 | 12/2004 |
| EP | 0 891 749 A1 | 1/1999 |
| GB | 374450 | 6/1932 |
| GB | 1442041 | 7/1976 |
| WO | WO 86/02259 A2 | 4/1986 |

* cited by examiner

*Primary Examiner* — Jeffrey Wollschlager
*Assistant Examiner* — Stella Yi
(74) *Attorney, Agent, or Firm* — Hodgson Russ LLP

(57) ABSTRACT

The invention relates to a device for production of dental molded parts from a polymerizable plastic, with a flask (16) and with a heating device (40) for heating the polymerizable plastic in the flask (16). The heating device (40) is movable relative to the flask (16).

8 Claims, 1 Drawing Sheet

DEVICE AND METHOD FOR PRODUCTION OF DENTAL MOLDED PARTS

CROSS-REFERENCE TO RELATED APPLICATIONS

This application claims foreign priority benefits under 35 U.S.C. §119(a)-(d) from German patent application ser. no. 10 2006 041 786.0 filed Sep. 6, 2006.

TECHNICAL FIELD

The invention relates to a device and method for production of dental molded parts from a polymerizable plastic, and more particularly to a device for production of dental molded parts from a polymerizable plastic, with a flask that can be filled with the polymerizable plastic via an injection device, and a heating device for heating the polymerizable plastic in the flask, the heating device being movable relative to the flask.

BACKGROUND OF THE INVENTION

Methods and devices of these kinds have been known of for many years, and reference may be made, for example, to U.S. Pat. No. 2,806,253. In this device for production of dental molded parts, a cuvette (or alternatively a flask) is heated by a heating coil after polymerizable material has been introduced into the flask. The heating effect is compensated by way of a cold water hose with which it is intended to permit a precise and targeted control of the polymerization.

In a slightly more recent development, as disclosed in British Patent 1,442,041 for example, the whole flask is briefly immersed in hot water, and intensive heat transfer is ensured by use of metals.

While the quality of the prostheses produced by the apparatus shown in British Patent 1,442,041 or other precision-molded parts made from plastic is good, it would be desirable to manage without additional equipment, such as the pressure pot provided for the hot water bath.

OBJECTS AND SUMMARY OF THE INVENTION

The object of the invention is therefore to make available a device for production of dental molded parts, which device and method permit improved and easier production of the dental molded parts, without the risk of uncontrolled polymerization of the polymerizable plastic that is introduced.

According to the invention, this object is achieved by providing a flask that can be filled with the polymerizable plastic via an injection device, and a heating device for heating the polymerizable plastic in the flask, the heating device being movable relative to the flask.

According to the invention, it is particularly expedient if the heating device as a whole can be removed from the flask. According to the invention, it is particularly expedient if the heating device is switched on or activated when the filling with polymerizable plastic has already taken place. This safely avoids polymerization taking place too early, and the possibility is afforded of starting the polymerization by switching on the heating device after filling is complete, or of preheating the heating device and then heating the flask in the heating position in which it is in thermally conductive contact with the heating device, and to do so preferably starting at a location that lies opposite the inlet opening for the plastic that is to be polymerized.

This solution has the advantage that, even when the heating device has already been heated, only the desired heat energy can be delivered, and arranging the heating device and inlet opening opposite one another ensures that no defective molded part is obtained as a result of heat shrinkage.

The heating device preferably interacts with one side of the flask that lies opposite an inlet opening of the flask. The flask can be held in any desired manner with or without clamping. For example, the two flask shells can be held together by a mechanical closure element before they are pressed more firmly onto one another by the clamping device.

The relative movement between flask and heating device is also not limited to the displaceability and/or pivotability of the heating device. While the pivoting of the heating device permits a rapid cooling of the flask, since the delivery of heat is then interrupted and cooling air can sweep along the outside of the heat transfer surfaces, it is also possible to remove the flask completely from the heating device.

The relative mobility between flask and heating device can be such that the flask is mounted fixedly on a receiving area of the housing and the heating device is mounted displaceably and/or pivotably on the housing. The movement of the flask can be effected with the aid of a drive device.

It is particularly expedient if the heating device has the shape of a U and encloses the outside of the flask. This on the one hand ensures uniform heating of the flask from one side, and, on the other hand, the separation between flask and heating device can be effected particularly easily. To this extent, the solution according to the invention makes it possible to combine the advantages of hot polymerization with its improved material quality and cold polymerization with its short processing time.

According to the invention, however, it is particularly expedient if the heating device can also be arranged lying opposite the inlet opening for the plastic material. This ensures that the polymerization initially takes place at parts of the flask that are remote from the inlet opening. To this extent, the chemical shrinkage during polymerization is automatically compensated by more material being pressed in. In this way it is possible to ensure an optimal fit of the prosthetic article in the mouth of the patient.

According to the invention, it is particularly expedient if, in the rest position, the flask can be delivered to the receiving area unimpeded and can be removed from it unimpeded.

According to the invention, it is particularly expedient if, in the heating position, the heating device at least partially encloses the flask, in particular in the manner of a U, and substantially from above, and in particular bears on the flask.

According to the invention, it is particularly expedient if the heating device is mounted on a housing, which comprises the receiving area and the heating device, and is mounted so as to be pivotable and/or displaceable, in particular with the aid of a drive device.

According to the invention, it is particularly expedient if the heating device has two branches which correspond substantially to the side branches of a U and which, if appropriate, diverge slightly from one another, and wherein in particular the branches of the heating device are pivotable relative to one another, and in particular can be pivoted apart for removal of the flask.

According to the invention, it is particularly expedient if the heating device has at least one reflector directed toward the flask.

According to the invention, it is particularly expedient if the heating device is arranged lying substantially opposite an inlet opening of the flask when the heating position is reached.

According to the invention, it is particularly expedient if the heating device has a heating element to which electrical energy is delivered.

According to the invention, it is particularly expedient if the heating element is formed by at least one electrical heating rod.

According to the invention, it is particularly expedient if the heating element generates hot air.

According to the invention, it is particularly expedient if, in a device, an inlet opening of the flask is surrounded by a heat insulator permitting heat insulation for the polymerizable plastic flowing in there compared to good heat-conducting areas of the flask, in particular the flask shells.

According to the invention, it is particularly expedient if, in a device the flask in particular has two flask shells which can be pressed onto one another with the aid of a clamping device, and in particular the two flask shells can be held together with the aid of at least one mechanical closure element.

According to the invention, it is particularly expedient if, in a device, the clamping device has at least one clamping lever, at least one clamping jaw interacting with a flask shell, and a clamp element, in particular in the form of a pneumatically and/or hydraulically and/or electrically operating clamp cylinder.

According to the invention, it is particularly expedient if the clamping lever is mounted pivotably in the housing, and, in particular, clamping jaws are articulated on its work arm, and the clamp element articulated on its power arm.

According to the invention, it is particularly expedient if the clamping device has two clamping levers which, each with a clamping jaw, press the two flask shells onto one another and jointly interact with a clamp element.

According to the invention, it is particularly expedient if the clamping device has a clamping frame on which at least one clamping lever is mounted, and the clamping lever is designed in particular as a one-arm lever.

According to the invention, it is particularly expedient if, in a device, the two free ends of the clamping levers interact with one another via a tie rod, in particular of a clamping frame.

According to the invention, it is particularly expedient if the flask can be filled with polymerizable plastic through the inlet opening substantially vertically from below, and if the polymerizable plastic can be pressed into the flask with the aid of an injection device. However, the filling can also be done in the horizontal direction or from the top downward.

According to the invention, it is particularly expedient if, in a device, an air release channel is arranged substantially opposite the inlet opening on the flask.

According to the invention, it is particularly expedient if, in a device, an underpressure can be established in the air release channel via a device for generating underpressure, in particular before the polymerizable plastic is pressed in.

According to the invention, it is particularly expedient if the device has a control unit for program control of the relative movement, the heating device and/or the clamp element and/or the heating of the heating device, the device that can be subjected to underpressure and/or the injection device.

According to the invention, it is particularly expedient if the flask can be inserted into a receiving area, and a heating device is movable relative to the flask and, in a heating position distanced from a rest position, the heating device heats the flask.

According to the invention, it is particularly expedient if the heating device is switched on after the filling operation and the flask is heated starting from its side lying opposite the inlet opening for the polymerizable plastic.

According to the invention, it is particularly expedient if the injection pressure is maintained while the heating device is switched on and the plastic is being polymerized, with the polymerization shrinkage being compensated in particular by more plastic being pressed in.

According to the invention, it is particularly expedient if the temperature of the flask is regulated electronically.

According to the invention, it is particularly expedient if the temperature is detected by a temperature sensor which is in direct or indirect contact with the flask.

According to the invention, it is particularly expedient if the temperature sensor is arranged on the device, in particular on the heating device.

According to the invention, it is particularly expedient if the temperature sensor is protected from the direct heat radiation of the heating device.

According to the invention, it is particularly expedient if the temperature sensor is pressed against the flask by the force of a spring.

According to the invention, it is particularly expedient if a clamping device presses the flask shells of the flask firmly onto one another before the injection of the polymerizable plastic, and in particular the clamping device is released only after the heating device has been switched off and the injection device has been switched off.

According to the invention, it is particularly expedient if the heating device, before being switched on, is pivoted and/or displaced from a rest position into a heating position and, after being switched off, is returned to the rest position.

According to the invention, it is particularly expedient if an air release channel, which is arranged essentially lying opposite the inlet opening on the flask, can be subjected to an underpressure, in particular before the injection of the polymerizable plastic.

BRIEF DESCRIPTION OF THE FIGURES

Further advantages, details and features will become clear from the following description of the invention with reference to the drawing, in which.

DETAILED DESCRIPTION

Figure 1:
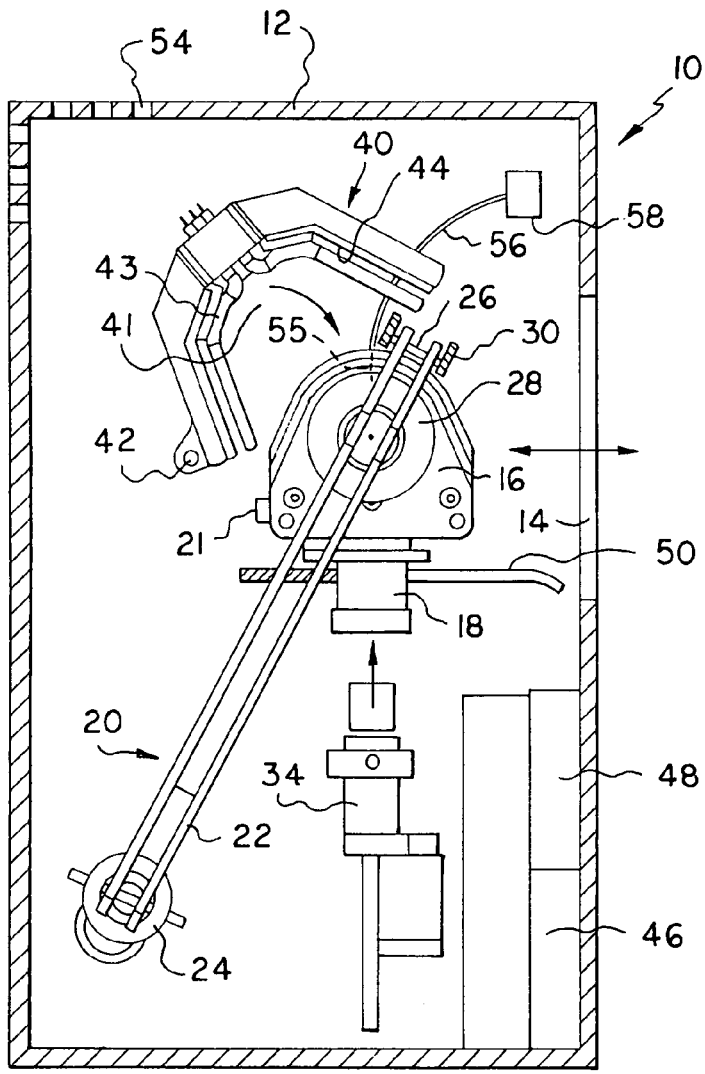
FIG. 1 shows a schematic view of a device according to the invention for production of dental molded parts, in one embodiment.
Figure 2:
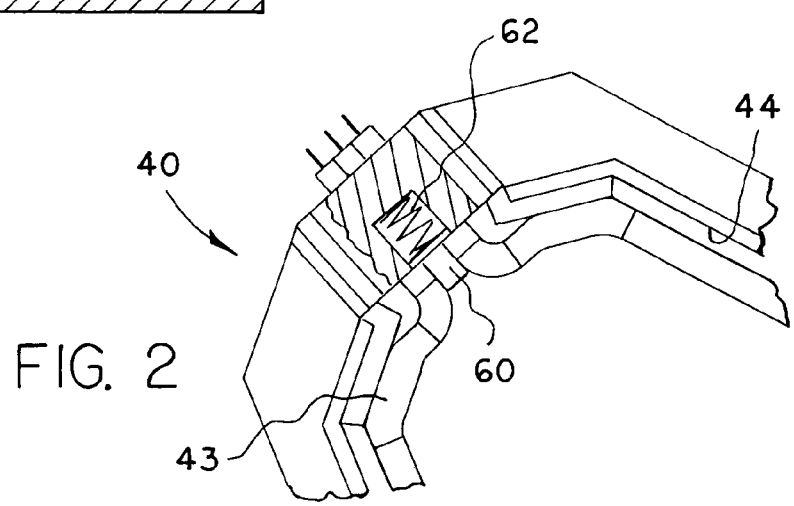
FIG. 2 is an enlarged detail view of a portion of FIG. 1.

The device 10 shown in FIG. 1, for production of dental molded parts from polymerizable plastic, comprises a housing 12 with a receiving area 41 for a flask 16. The housing 12 accommodates the flask 16, which is mounted just behind a service opening 14, the flask 16 being intended for the injection molding of a dental molded part such as a prosthesis. The flask 16 is made up of two flask shells which, in the illustrative embodiment shown, are held together by a clamping mechanism 21 and can be pressed onto one another by a clamping device 20. For this purpose, the clamping device 20, which is also received in the housing 12, has two clamping levers 22 which can be actuated via a clamp cylinder 24 as clamp element. Only one of the two clamping levers 22 is shown in FIG. 1, the other one being arranged behind the plane of the drawing.

The clamping levers 22 are mounted pivotably about a pivot axle 26, and, adjacent to the pivot axle 26, there are clamping jaws 28 which press on the flask shells. The pivot axles 26 are each mounted rigidly in the housing.

Although the clamping levers 22 are designed here as a one-arm lever, it will be appreciated that, instead of this, a two-arm lever is also possible.

A tie rod 30, articulated on each pivot axle 26, extends between the two clamping levers and takes up the tensile forces acting on the free ends of the clamping levers 22.

Because of the considerable lever step-down ratio, a considerable pressure can be exerted on the flask shells via the clamp cylinders 24, said pressure can be from 2000 N to 25000 N, in particular a pressure of between 5000 N and 15000 N.

The flask 16 has a downwardly open inlet opening 18 which interacts with an injection device 34 that extends beneath the inlet opening 18 and has a vertically movable plunger. With the aid of the injection device 34, the polymerizable plastic can be pressed into the hollow cavity of the flask 16. The injection device 34 has a pressure cylinder suitable for this purpose.

The flask 16 can be moved from the rest position shown in FIG. 1 to a heating position. The heating device 40 for this purpose has a heating element 43 whose thermal energy is delivered to the flask 16 via a reflector 44. The heat is preferably transmitted by heat radiation, it being understood that a good heat transmission can also be achieved by direct thermal contact.

Whereas the flask 16 has in principle a stable metal housing, which for example can also be made of aluminum, the area of the inlet opening 18 at least is made of heat-insulating but heat-resistant material.

According to the invention, the heating device 40 extends so as to match the top outer face of the flask 16. The heating device 40 is mounted pivotably on a pivot axle 42 of the housing. It can be mounted in such a way that, in the non-active state shown in FIG. 1, the flask 16 is freely movable when the clamping device 20 is released and it can be removed, for example, through the service opening 14. By contrast, the heating device 40 can also be pivoted into a position in which it is active and in which it encloses the flask 16 along the latter's top face and its oblique lateral flanks. In doing so, the heating device 40 can also bear directly on the metal of the flask 16. The flask 16 is thus clamped in the clamping device 20.

Starting from the lateral service opening 14 in the housing 12, a guide rail 50 for the flask extends as far as the receiving area 41.

The heating device 40 and the clamp cylinder 24 are controlled via a control unit 46 which is accommodated in the housing 12. The device according to the invention can also be controlled via an operating arrangement 48 also arranged on the housing.

According to the invention, it is proposed that the heating device 40 is switched off after completion of the injection operation and is then pivoted aside a few seconds later so that the flask 16 can cool down. The heating device 40 is then always still slightly warm.

According to the invention, the pivoting of the heating device has to take place only by a small amount, for example 20° to 50° and preferably about 35°. This is sufficient for the thermal and spatial separation of the flask 16 and for easy removal of the flask 16.

Ventilation slots 54 are provided in the housing. These are necessary so that hot air can leave the inside of the housing 12.

An air release channel, indicated by the broken line 55, is arranged lying substantially opposite the inlet opening 18 on the flask 16. An underpressure can be established in the air release channel 55 via a device 58 for generating an underpressure, in particular before the polymerizable material is pressed in, the device being connected to the air release channel 55 via an under pressure line 56. This is more fully described in U.S. Pat. No. 7,578,667 filed concurrently with this application, the subject matter of which is incorporated herein by reference thereto.

The temperature of the flask 16 is regulated electronically. To this end the temperature is detected by a temperature sensor 60 which is in direct or indirect contact with the flask 16. The temperature sensor 60 is arranged on the heating device 40, and may be pressed against the flask 16 by the force of a spring 62.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A method for production of dental molded parts from a polymerizable plastic, comprising the following steps:
   providing:
   a housing;
   a flask mounted to the housing including two shells that can be filled with polymerizable plastic, the flask having opposed sides, one of the opposed sides having an inlet opening, and the other of the opposed sides having a heatable top outer face,
   an injection device,
   a clamping device for pressing the shells firmly onto one another before injection of the polymerizable plastic, and
   a heating device mounted to the housing for heating the polymerizable plastic in the flask, the heating device and the flask being movable relative to each other;
   pressing the polymerizable plastic with the injection device into the flask through the inlet opening of the flask with a suitable injection pressure until the flask is filled while the flask is mounted to the housing;
   moving the heating device and the flask relative to one another while the flask is mounted to the housing after the flask is filled with the polymerizable plastic from a rest position where the flask is spaced away from the heating device to a heating position where the flask is in contact with the heating device, wherein the heating device encloses the heatable top outer face of the flask while the flask is in contact with the heating device and has a shape that matches a shape of the heatable top outer face; and
   heating the flask with the heating device when the flask is in the heating position to cause the polymerizable plastic within the flask to polymerize by heat radiation.

2. The method as claimed in claim 1, wherein the heating device is switched off after the polymerization and is moved into its rest position.

3. The method as claimed in claim 1, wherein the clamping device presses the shells of the flask firmly onto one another before injection of the polymerizable plastic, and wherein the clamping device is released only after the heating device has been switched off and the injection device has been switched off.

4. The method as claimed in claim 1, wherein the injection pressure is maintained while the heating device is switched on and the polymerizable plastic is being polymerized, with the polymerization shrinkage being compensated by more of the polymerizable plastic being pressed in.

5. The method as claimed in claim 1, wherein the injection of the polymerizable plastic into the flask and/or the heating of the flask starts after the clamping device is activated.

6. The method as claimed in claim 1, wherein the flask is subjected to an underpressure through an air channel before and when the polymerizable plastic is being pressed into the flask.

7. The method as claimed in claim 1, wherein the flask is removably mounted to the housing.

8. The method as claimed in claim 1, wherein the moving of the heating device and the flask relative to one another while the flask is mounted to the housing uses a drive device.

* * * * *